(12) United States Patent
Wuthrich et al.

(10) Patent No.: US 6,319,520 B1
(45) Date of Patent: Nov. 20, 2001

(54) SOLID THERMOFORMABLE CONTROLLED-RELEASE PHARMACEUTICAL COMPOSITION

(75) Inventors: Patrick Wuthrich, Orleans; Hervé Rolland, Olivet; Gilles Briault, Orleans; Gérald Pichon, Orleans; François Tharrault, Orleans, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/604,500

(22) Filed: Jun. 27, 2000

(30) Foreign Application Priority Data

Jun. 28, 1999 (FR) .................................... 99 08210

(51) Int. Cl.[7] .............................. A61K 9/32; A61K 9/20; A61K 9/22; A61K 47/32
(52) U.S. Cl. ......................... 424/482; 424/464; 424/468; 514/772.4
(58) Field of Search ................... 424/464, 468, 424/489, 490, 482; 514/772.4

(56) References Cited

U.S. PATENT DOCUMENTS 5,102,668 * 4/1992 Eichel et al. ..................... 424/490

FOREIGN PATENT DOCUMENTS

WO 96/14058 * 5/1996 (WO).

OTHER PUBLICATIONS

Rohm America—Eudragit Pharma Coatings, one page, dated Jun. 5, 2000.
Rohm America—EUDRAGIT® Products and Market Applications, one page, dated Jun. 5, 2000.
Rohm America—Eudragit, Methacrylate Monomers, Methacrylate Polymers, one page, dated Jun. 5, 2000.

* cited by examiner

Primary Examiner—Thurman K. Page
Assistant Examiner—Rachel M. Bennett
(74) Attorney, Agent, or Firm—The Firm of Hueschen and Sage; G. Patrick Sage

(57) ABSTRACT

The present invention relates to a new solid controlled-release pharmaceutical composition obtained by thermoforming, in the hot state, a mixture based on polymers belonging to the polymethacrylate family and medicinal active ingredient(s).

35 Claims, 7 Drawing Sheets

Figure 1:
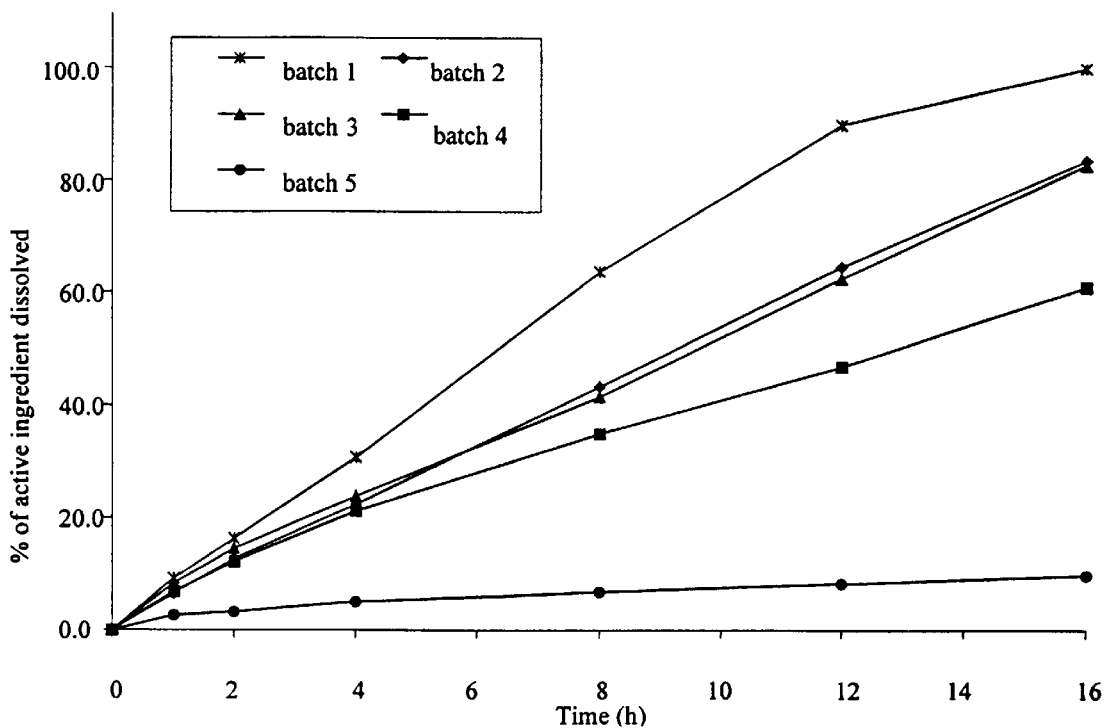

*In vitro* dissolution kinetics of batches 1 to 5 produced by extrusion of a benfluorex hydrochloride/polymethacrylate mixture (50/50)

*In vitro* dissolution kinetics at pH 2 of compositions produced by extrusion of a fenspiride hydrochloride/Eudragit® RLPO (50/50) mixture or a fenspiride hydrochloride/Eudragit® E100 (30/70) mixture

*In vitro* dissolution kinetics of the composition of Example 7 produced by extrusion

Dissolution kinetics of the composition of Example 7, administered by the oral route, in humans (n = 12)

SOLID THERMOFORMABLE CONTROLLED-RELEASE PHARMACEUTICAL COMPOSITION

FIELD OF THE INVENTION

The present invention relates to a new solid controlled-release pharmaceutical composition obtained by thermoforming, in the hot state, a mixture based on polymer (s) belonging to the polymethacrylate family and medicinal active ingredient(s).

Numerous pharmaceutical compositions intended for the controlled release of pharmaceutical active ingredients have been proposed and produced, for administration by the oral, buccal, sublingual, ocular, rectal, vaginal and/or parenteral routes. The objectives of those new compositions were essentially:

- to reduce the frequency of administration of the medicaments,
- to obtain relatively constant levels of active ingredient in the target medium or biological site,
- to obtain release profiles matching the pharmacological activity of the medicaments.

The principle most commonly employed for controlling release is to incorporate the active ingredient(s), together with excipients, which most often are polymeric in nature, in matrices.

Whatever the matrix compositions envisaged, their production is beset by specific problems of manufacture:

- a manufacturing process that is complex and composed of several steps,
- problems of stability of the active ingredient during the manufacturing process and in relation to the excipients used,
- problems in the fine control of the rate of release of the active ingredient(s), which is often variable over time and dependent for example on the particle size of the batches of polymers with compression processes,
- a manufacturing process that allows a pharmaceutical form to be obtained which is essentially suited to just one route of administration,
- difficulty in achieving reproducibility of the batches due to the multiplicity of steps.

The present invention is an alternative thereto that, by using techniques of thermoforming, allows the difficulties of a general nature described hereinbefore to be overcome to obtain solid pharmaceutical compositions that allow the controlled release of medicinal active ingredient(s). It especially allows the number of steps in the production of final galenical forms to be reduced, thereby limiting the problems of reproducibility and the economic cost, as well as ensuring savings of time and space within a chain of production.

More especially, the invention is directed to a new application of polymethacrylates in the production of the said solid pharmaceutical compositions without addition of plasticiser and without addition of agents that modify the release of the active ingredient(s). The invention, as accomplished by the inventors, accordingly allows the number of products involved in a galenical formulation to be restricted, thereby limiting the problems of stocking and of supply, as well as the problems associated with management of the environment.

PRIOR ART DESCRIPTION

Thermoforming in the hot state relates especially to the techniques of extrusion, co-extrusion, injection and co-injection. These different techniques are well known in the field of plastics and have been widely used in the automobile and packaging sectors.

Because of their characteristics, and the physicochemical properties of the polymers that can be used for thermoforming, the said techniques, and especially simple extrusion, are increasingly being applied in the field of formulating active ingredients.

Various patents accordingly describe controlled-release pharmaceutical compositions which are obtained by extrusion of a mixture comprising at least one active ingredient, one or more extrudable and pharmaceutically acceptable polymers, one plasticiser and/or one retardant, the latter compound allowing the release of the active ingredient to be modified.

In particular, Patent Application WO 96/14058 claims a pharmaceutical composition including especially as therapeutic agent an opioid, which is dispersed in a matrix produced by extrusion. The matrix for extrusion therefore comprises an active ingredient, a hydrophobic material which can be melted, such as an alkylcellulose or an acrylic or methacrylic polymer, and a hydrophobic material, such as a fatty acid or a fatty alcohol. The latter compound serves as retardant and allows the release of the said active ingredient to be slowed down and controlled. A plasticiser is added to the mixture for the purpose of reducing the extrusion temperature.

U.S. Pat. No. 5,102,668 describes a pharmaceutical composition for controlled release which is independent of the pH, the said composition being obtained by wet extrusion of polymers such as polymethacrylates, the said polymers being hydrophilic at low pH and hydrophobic at high pH. The polymethacrylate preferably used is Eudragit® E100. The extrudates thereby obtained must subsequently undergo a spheronisation step and then, advantageously, they are covered with a polymer film composed of Eudragit® NE 30 D. The association between the polymer comprising the extrudate and the polymer comprising the coating film allows the particular technical problem of that invention to be solved, namely control of the release of the active ingredient as a function of the pH of the dissolution medium.

Among the prior art there may also be mentioned the patent DE 41 38 513, which presents a process for the preparation of a controlled-release pharmaceutical composition by continuous extrusion of a mixture comprising at least one active ingredient, a polymethacrylate, and a polymer of N-vinylpyrrolidone and/or of hydroxyalkyl (methyl) cellulose. The latter compounds are used as plasticisers and play a role in regulating the controlled release of the active ingredient.

The article *Pharm. Res.* 1996, 13 (5), 804–808, also describes the hot extrusion of Eudragit® E 100, to which a plasticiser (at least 12% triethyl citrate) has been added, for obtaining films allowing the controlled release of active ingredients.

Similarly, the journals *J. Cont. Rel.* 1995, 36, 243–250 and *Drug Dev. Ind. Pharm.* 1994, 20, 1323–1339 report the use of Eudragit® RS PM, to which a plasticiser (triacetin) has been added, for obtaining granules by hot extrusion. The active ingredient release kinetics are rapid and the granules do not release all the active ingredient. The extrusion temperatures are located in the range from 130° C. to 140° C.

Those various documents therefore describe the application of the technique of simple extrusion for obtaining new pharmaceutical compositions. The techniques of injection and co-injection have been much less studied and principally concern solid pharmaceutical compositions wherein the matrix is based on cellulose derivatives, starch or polyethylene glycol.

Finally, with regard to the technique of co-extrusion, Patent Application FR 2 766 088 describes a process for the production of an article from which it is possible to manufacture controlled-release devices, the said process comprising carrying out co-extrusion of polymer and active ingredient, the polymer used being preferably an organosilicate compound capable of cross-linking in the presence or absence of a cross-linking agent.

DETAILED DESCRIPTION OF THE INVENTION

The present invention allows, in a simple and economical manner, a solid controlled-release pharmaceutical composition to be obtained directly, by simple mixture of one or more active ingredient(s) and of polymer(s) that have plastic properties and are pharmaceutically acceptable, without addition of plasticiser or retardant, the said mixture being thermoformed. The control of the release of active ingredient in the said composition is obtained solely by means of judicious selection of the plastic polymer(s) used and of the amount thereof relative to that of the active ingredient(s). Besides the fact that the pharmaceutical composition according to the invention is new, it allows galenical forms to be obtained that are easily adaptable to various active ingredients and to their best mode of administration and that ensure controlled and reproducible release of the said active ingredients.

One of the objects of the invention was to achieve a solid controlled-release pharmaceutical composition comprising a simple mixture of active ingredient(s), and of polymer(s) having plastic properties, the said polymer(s) being composed of the group of the polymethacrylates, without addition of plasticiser and/or retardant, and without use of solvent.

Surprisingly, the solid pharmaceutical compositions of the inventors can, because of their specific make-up, be subjected to the technique of extrusion, co-extrusion and also of injection or co-injection equally well. Employing the said techniques results in matrices being obtained in forms that have a size and geometry appropriate for various routes of administration, such as, especially, the oral, buccal, sublingual, ocular, vaginal, rectal and parenteral routes. This advantage of the pharmaceutical compositions of the present invention makes it possible to envisage manufacture, starting from the same starting material, of the galenical formulation best suited to the active ingredient incorporated in the said composition and, at the same time, to the most appropriate administration route for the characteristics of the said active ingredient and the population having to use the formulations.

Another object of the invention was to obtain a solid pharmaceutical composition wherein the matrix would be adaptable to a wide range of active ingredients having very different physicochemical characteristics, for example lipophilic or hydrophilic therapeutic agents or chemically unstable therapeutic agents.

Finally, one of the objects of the invention was to obtain a solid pharmaceutical composition wherein it would be possible, by simply adapting the amounts of active ingredients and plastic polymers used, to modify the release of active ingredient by simple means.

More specifically, the present invention relates to a solid controlled-release pharmaceutical composition, administrable especially by the oral route, comprising a thermoformable mixture of at least one active ingredient and one or more polymers selected from the group of the polymethacrylates, the controlled release of the active ingredient(s) being ensured solely by the chemical nature and the amount of the polymethacrylate(s) used, and the technique employed for manufacture of the said composition.

A controlled-release pharmaceutical composition is understood to be one that releases the active ingredient(s) over a period of from several minutes (corresponding to immediate release) to a period of more than 20 hours (corresponding to prolonged release), it being possible for the said release to take place in a manner that is delayed in time after administration of the composition. In the case of delayed-release pharmaceutical compositions, the lag-time (corresponding to the time between administration of the said composition and release of the active ingredient) can be a period of from 30 minutes to 8 hours, it being possible for the release of the active ingredient thereafter to be immediate release or prolonged release as defined hereinbefore. Within the context of the invention, it is possible to obtain pharmaceutical compositions which show release profile combination like a immediate release of a part of the active ingredient(s) followed by one or more delayed-release.

A polymethacrylate is understood to be a copolymer of methacrylic acid corresponding to a fully polymerised copolymer of methacrylic acid and acrylic or methacrylic ester. The said polymethacrylates are commonly referred to by the name Eudragit® and can be presented in the form of a powder or granules.

A thermoformable mixture is understood to be a mixture capable of undergoing transformation under the combined effect of heat and the shearing forces of an endless screw, for example the techniques of extrusion, co-extrusion, injection and co-injection.

Among the various Eudragit® products commercially available, those preferably used within the context of the invention are Eudragit® RL and RS, which refer to copolymers of ammonium methacrylate that consist of fully polymerised copolymers of acrylic acid and methacrylic acid ester having a small amount of quaternary ammonium groups.

The said Eudragit® products correspond to the general formula (I):

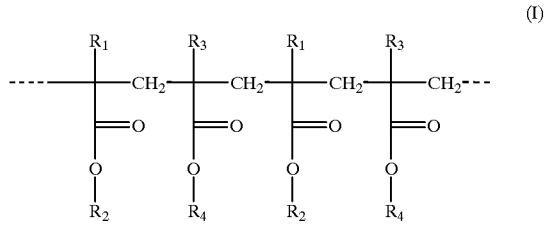

wherein:
$R_1$ represents a hydrogen atom or a methyl group,
$R_2$ represents a methyl or ethyl group,
$R_3$ represents a methyl group,
and $R_4$ represents a group $CH_2$—$CH_2$—$N_{\oplus}(CH_3)_3$, $Cl^{\ominus}$.

Especially advantageously, the Eudragit® products used in the thermoformable mixture of the invention are Eudragit® RLPO and/or RSPO, which correspond to poly (ethyl acrylate, methyl methacrylate, trimethylaminoethyl methacrylate chloride)'s in the relative proportions of 1:2:0.2 and 1:2:0.1, respectively.

According to another advantageous variant of the invention, the thermoformable mixture of the invention can comprise Eudragit® of type E. This polymer corresponds to a poly(butyl methacrylate, (2-dimethylaminoethyl) methacrylate, methyl methacrylate) in the relative proportions of 1:2:1. Eudragit® of type E can be used as the sole polymethacrylate polymer in the thermoformable mixture or can be used in association with Eudragit® RLPO and/or RSPO.

Among the Eudragit® products of type E, special mention may be made of Eudragit® E 100, the particular feature of which is that it is soluble at pH's of less than 5, allowing rapid release of the active ingredient in the stomach. As a result of that fact, the use of Eudragit® of type E, and more especially of type E100, is especially well suited to obtaining immediate-release solid pharmaceutical compositions that are administered by the oral route.

According to a third variant of the invention, the thermoformable mixture of the invention can comprise Eudragit® of type L100, L100-55 and/or S100. Eudragit® L100 corresponds to a poly(methacrylic acid, methyl methacrylate) in the relative proportions of 1:1. Eudragit® L100-55 corresponds to a poly(methacrylic acid, ethyl acrylate) in the relative proportions of 1:1. Eudragit® S100 corresponds to a poly(methacrylic acid, methyl methacrylate) in the relative proportions of 1:2. These types of Eudragit® can be used as the sole polymethacrylate polymer in the thermoformable mixture or can be used in association with one or more of the other types of Eudragit® mentioned hereinbefore. These polymethacrylates are soluble at pH's of more than 5.5, thereby allowing release of the active ingredient in the intestine and/or colon. Use of the said Eudragit® products is especially valuable in obtaining gastro-resistant solid controlled-release pharmaceutical compositions.

The pharmaceutical compositions thereby obtained within the context of the invention allow, unexpectedly, controlled release of the active ingredient(s) to be obtained over a period of from several minutes to more than 20 hours, it being possible for that release to be linear depending on the active ingredient incorporated, the make-up of the matrix and the technique employed.

The pharmaceutical compositions of the invention are therefore obtained by mixture of at least one active ingredient and one or more polymethacrylate polymers, lowering of the viscosity of the said mixture under the effect of heat and the shearing forces of an endless screw inside a barrel, and then treatment of the melted mixture by one of the following means:

expulsion from the extruder through a calibrated orifice of variable size and shape, the material obtained being subsequently cut according to the desired final shape of the matrix; this constitutes the technique of simple extrusion;

or the first extruder containing the said mixture of reduced viscosity described hereinbefore is associated with a second extruder containing a mixture comprising
* either, solely, one or more polymethacrylate(s) for the control of the release of the active ingredient(s) from the central portion,
* or one or more polymethacrylate(s) in admixture with one or more active ingredient(s), which may be the same as or different to that (or those) contained in the central portion, each extruder operating continuously and feeding the same orifice;

the orifice allows the passage of the mixture coming from the first extruder, ensuring the formation of the inner layer of the final matrix, and also the passage of the mixture coming from the second extruder, ensuring the formation of the outer layer of the final matrix; the extrudate thereby obtained is then cut according to the desired final shape and may optionally undergo moulding; the ends of the extrudate may optionally be closed by means of an appropriate technology; this constitutes the technique of co-extrusion;

or injection under pressure, within a press, into moulds having a shape and volume perfectly defined according to the geometric characteristics desired for the matrix; this constitutes the technique of injection;

or the press is equipped with a plurality of injection units allowing injection into one and the same mould, sequentially or simultaneously, of at least two mixtures, which may be the same or different; the first injection unit injects the said mixture, described hereinbefore, which constitutes the central portion, or heart, of the matrix; the second injection unit injects, at the periphery of the central portion, an outer layer of a mixture comprising:
* either, solely, one or more polymethacrylate(s) for the control of the release of the active ingredient(s),
* or one or more polymethacrylate(s) in admixture with one or more active ingredient(s), which may be the same as or different to that (or those) contained in the central portion;

this constitutes the technique of co-injection, which at the same time encompasses the techniques of multi-component injection and of "sandwich" injection.

According to the technique employed, it is therefore possible, within the context of the present invention, to obtain solid controlled-release pharmaceutical compositions that are administrable especially by the oral, buccal, sublingual, ocular, rectal, vaginal or parenteral routes, that are of variable size and geometry, are mono-layered or multi-layered and are best suited to the most appropriate release profiles for each therapeutic agent.

The pharmaceutical compositions may be used directly, without another transformation technique being performed apart from packaging. If desired, however, the said pharmaceutical compositions may undergo transformation by grinding or granulation for introduction into a gelatin capsule or for compression or may be subjected to coating.

The pharmaceutical compositions of the invention may optionally also comprise pharmacologically acceptable excipients selected, for example, from the group of anti-oxidants, flavourings, colourings, preservatives, sweeteners and anti-adherents.

The thermoforming temperature is from 60° C. to 150° C. The temperature is preferably from 80° C. to 130° C.

Among the active ingredients incorporated in the composition according to the invention, there may be mentioned, without implying any limitation, penicillins, cephalosporins, cyclines, beta-lactamase inhibitors, aminosides, quinolones, nitroimidazole compounds, sulphamides or antibacterials, antihistamines, anti-allergics, anaesthetics, steroidal or non-steroidal anti-inflammatories, antalgics having local or systemic action, antispasmodics, anti-cancer agents, diuretics, beta-blockers, antihypertensives, anti-angina agents, anti-arrythmics, vasodilators, bradycardiacs, calcium inhibitors, sedatives, cardiotonics, antifungals, anti-ulcerative agents, venotonics, vasculoprotectors, anti-ischaemics, anti-emetics, anticoagulants, antithrombotics, immunosuppressors, immunomodulators, antivirals, antidiabetics, hypolipidaemic agents, anti-obesity agents, anticonvulsants, hypnotics, antiparkinsonian agents, antimigraine agents, neuroleptics, anxiolytics, antidepressants, antipsychotics, psychostimulants, memory-enhancers, bronchodilators, antitussives, anti-osteoporotics, peptide hormones, steroids, enzymes, enzyme inhibitors, and melatoninergic agonists and antagonists.

The Examples that follow illustrate the invention but do not limit it in any way.

EXAMPLE 1

The compositions of Example 1 are obtained by the technique of extrusion. They all contain 125 mg of active ingredient, namely benfluorex hydrochloride. The compositions are composed of a mixture comprising 50% active ingredient and 50% polymethacrylate. Example 1 shows the influence of the nature of the polymethacrylates used on the in vitro dissolution kinetics of the active ingredient. In batches 1 to 5, which have a constant weight of polymethacrylates, the amount of Eudragit® RLPO relative to that of Eudragit® RSPO accordingly varies from 100 to 0%.

When Eudragit® RSPO is absent from the mixture, release of the active ingredient is observed over a period of 16 hours. The addition of a small amount of Eudragit® RSPO allows the benfluorex release rate to be controlled.

TABLE 1

Variation of the Eudragit ® RLPO/RSPO ratio
of a composition containing 125 mg of benfluorex hydrochloride

| Polymethacrylate | Batches | | | | |
|---|---|---|---|---|---|
| (50% of the composition) | 1 | 2 | 3 | 4 | 5 |
| Eudragit ® RLPO (in %) | 100 | 90 | 75 | 50 | 0 |
| Eudragit ® RSPO (in %) | 0 | 10 | 25 | 50 | 100 |

The in vitro dissolution kinetics are presented in the annexed FIG. 1.

EXAMPLE 2

The compositions of Example 2 are obtained by the technique of extrusion. They all contain 3.2 mg of active ingredient, namely rilmenidine dihydrogen phosphate. The compositions are composed of a mixture comprising 10% active ingredient and 90% polymethacrylate.

Example 2 confirms the observations obtained in Example 1 relating to the influence of the nature of the polymethacrylates used on the in vitro release of the active ingredient. Control of the release of the active ingredient is obtained by variation of the amount of Eudragit® RLPO relative to that of Eudragit® RSPO.

TABLE 2

Variation of the Eudragit ® RLPO/RSPO ratio
of a composition containing 3.2 mg of rilmenidine dihydrogen phosphate

| Polymethacrylate | Batches | | | |
|---|---|---|---|---|
| (50% of the composition) | 6 | 7 | 8 | 9 |
| Eudragit ® RSPO (in %) | 100 | 90 | 75 | 50 |
| Eudragit ® RLPO (in %) | 0 | 10 | 25 | 50 |

Figure 2:
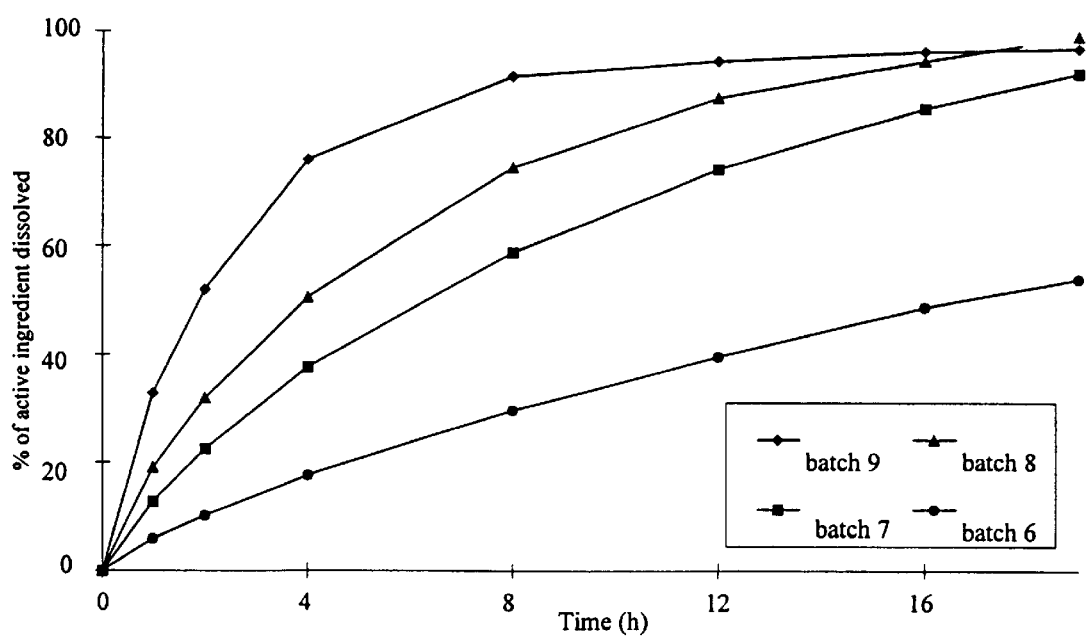

The in vitro dissolution kinetics are presented in the annexed FIG. 2.

EXAMPLE 3

The composition of Example 3 is obtained by the technique of extrusion. It contains 150 mg of active ingredient, namely fenspiride hydrochloride. The composition is composed of a mixture comprising 30% active ingredient and 70% polymethacrylate, the latter being solely Eudragit® RLPO.

Figure 3:
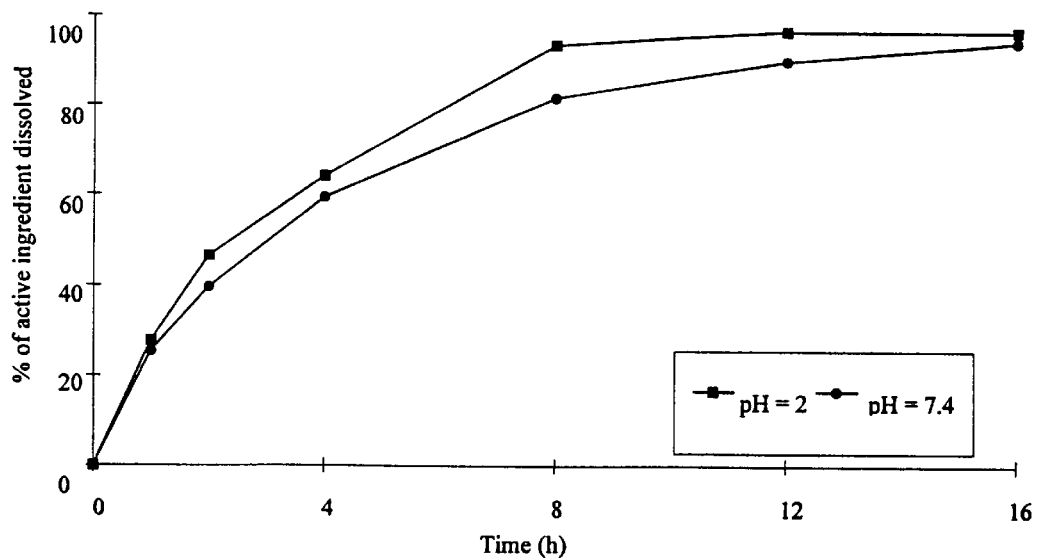

Example 3 shows the weak influence of the pH of the dissolution medium on the release kinetics of the active ingredient, as illustrated in FIG. 3 (annexed) which shows the dissolution profile at pH=2 and the dissolution profile at pH=7.4.

The in vitro dissolution kinetics are presented in the annexed FIG. 3.

EXAMPLE 4

The compositions of Example 4 are obtained by the technique of extrusion. They contain 150 mg of active ingredient, namely fenspiride hydrochloride. The compositions are composed of a mixture comprising 30% active ingredient and 70% polymethacrylate, the latter being either Eudragit® RLPO or Eudragit® E100. Example 4 shows much more rapid release at pH 2 with Eudragit® E100 than with Eudragit® RLPO.

Figure 4:
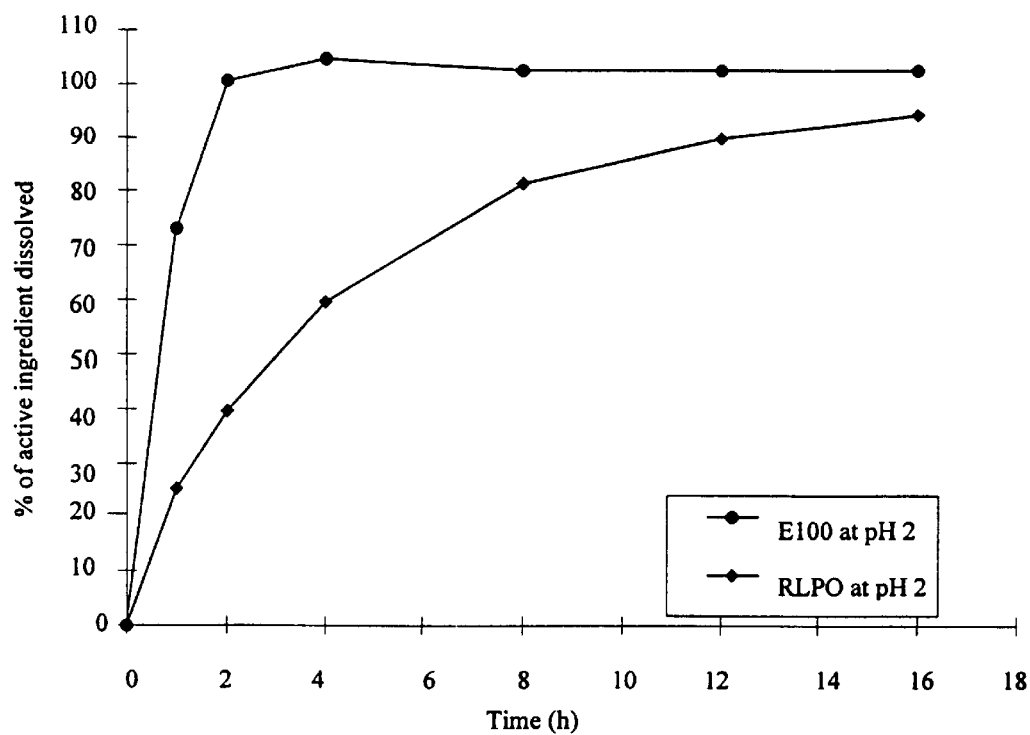

The in vitro dissolution kinetics are presented in the annexed FIG. 4.

EXAMPLE 5

The composition of Example 5 is obtained by the technique of injection. It contains 135 mg of active ingredient, namely benfluorex hydrochloride. The composition is composed of a mixture comprising 50% active ingredient and 50% polymethacrylate, the latter being Eudragit® RLPO. The release of the active ingredient as a function of time is linear over 6 hours with zero-order kinetics.

Figure 5:
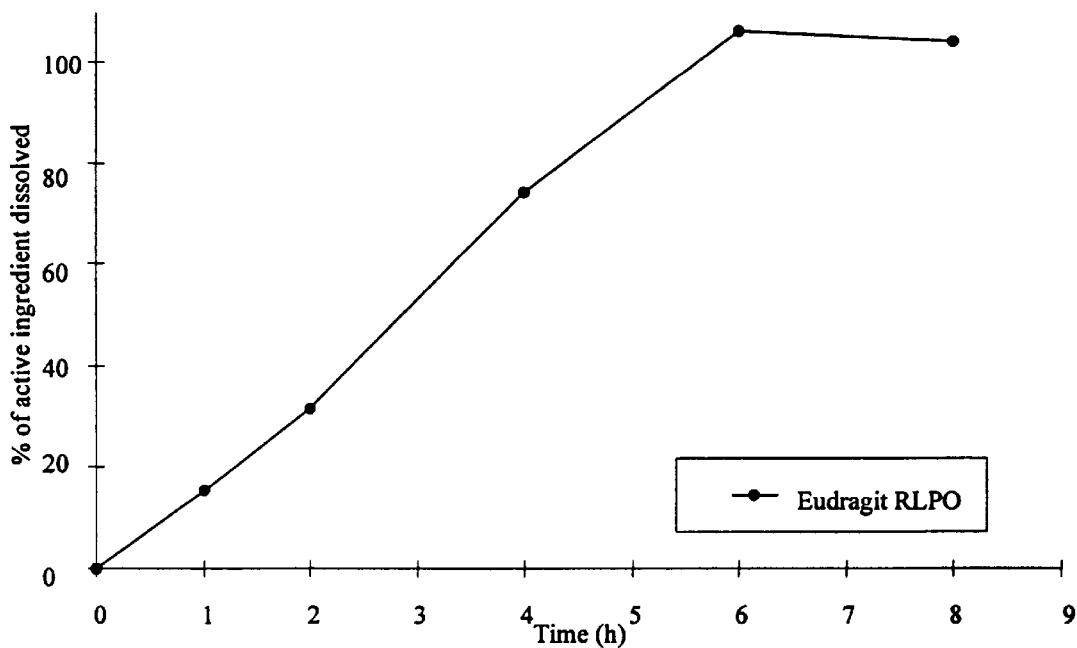

The in vitro dissolution kinetics are presented in the annexed FIG. 5.

EXAMPLE 6

The compositions of Example 6 are obtained by the technique of co-extrusion. They all contain 135 mg of active ingredient, namely fenspiride hydrochloride. The inner layer is composed of a mixture of 30% fenspiride and 70% Eudragit® RLPO. The outer layer is composed of 100% Eudragit® RLPO.

The presence of an outer layer of RLPO polymethacrylate allows the kinetics of release of the active ingredient from the inner layer to be slowed down.

Increasing the thickness of the outer layer from 0.1 mm to 0.4 mm allows the kinetics of release of the active ingredient to be slowed down even more and to obtain a "lag-time" or latency time of about 4 hours before the release of the active ingredient.

Figure 6:
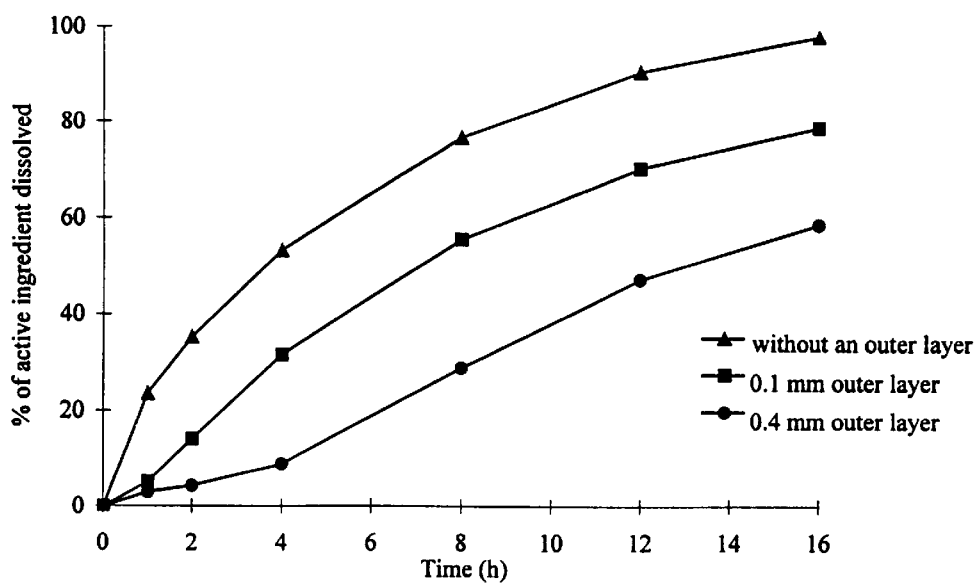

The in vitro dissolution kinetics are presented in the annexed FIG. 6.

EXAMPLE 7

The composition of Example 7 is obtained by the technique of extrusion. It contains 59 mg of active ingredient, namely (1R)-1-({-[[(2R)-2-(acetylamino)-3-phenylpropanoyl](cyclopentyl)amino]acetyl}amino)-4-{[amino(imino)methyl]amino}butylboronic acid hydrochloride. The composition is composed of a mixture comprising 59% active ingredient and 41% polymethacrylate, the latter being Eudragit® RLPO.

Figure 7:
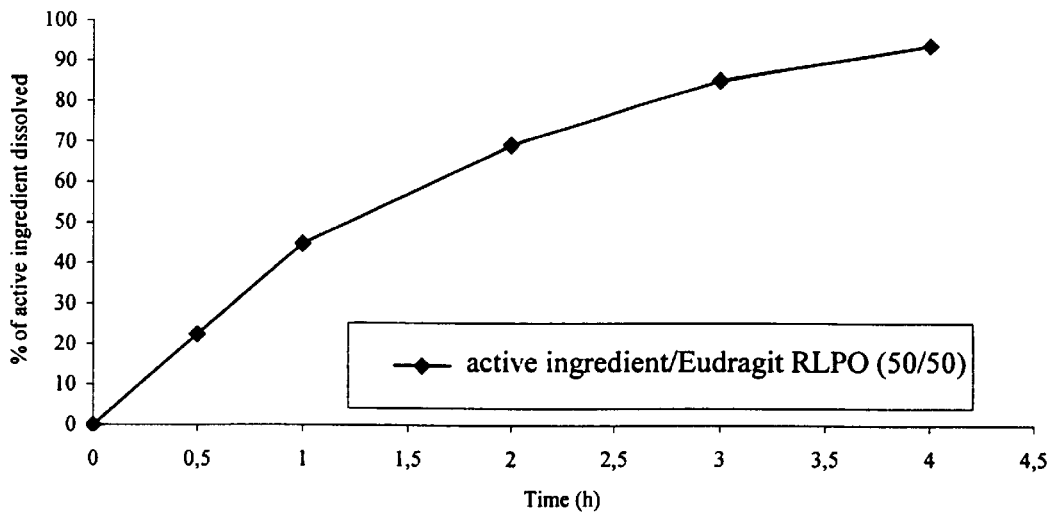

The in vitro release of the active ingredient is prolonged over four hours (FIG. 7). The results of plasma levels obtained in humans (n=12) after administration by the oral route of an extrudate containing 59 mg of the said active ingredient are presented in FIG. 8.

Figure 8:
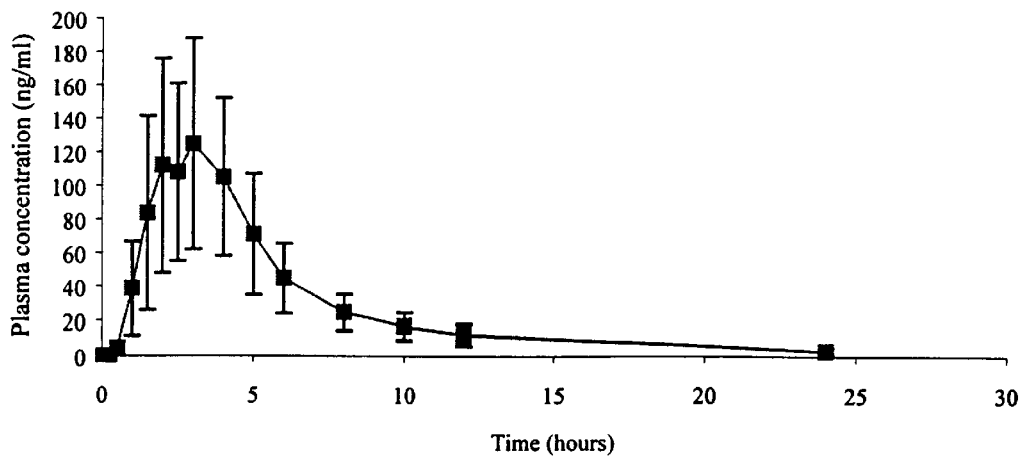

FIGS. 7 and 8 are presented in the annex.

EXAMPLE 8

In the same manner as in Example 1. different compositions composed of a 1/1 active ingredient/polymethacrylate mixture were obtained with various active ingredients. The compositions contain the following amounts of active ingredient:

gliclazide . . . 30 mg piribedil . . . 50 mg 2-({2-methoxy-2-[3-(trifluoromethyl)phenyl]ethyl}amino)ethyl-4-2(2-{[2-(9H-fluoren-9-yl)acetyl]amino}ethyl)benzoate L-tartrate . . . 200 mg 3a,10-dihydro-5,5-dioxo-4H-(S)-pyrrolidino[1,2-c][1,2,4]benzothiadiazine . . . 100 mg N-[2-(5-ethyl-1-benzothien-3-yl)ethyl]acetamide . . . 100 mg As in Example 1, it is observed with these different compositions that variation of the amount of Eudragit® RSPO relative to that of Eudragit® RLPO makes it possible for the active ingredient release rate to be varied and therefore to be controlled as required.

EXAMPLE 9

In the same manner as in Example 2, different compositions composed of a 1/9 active ingredient/polymethacrylate mixture were obtained with various active ingredients. The compositions contain the following amounts of active ingredient:

indapamide . . . 1.5 mg tertatolol hydrochloride . . . 5 mg

Control of the release of the active ingredient is obtained by variation of the amount of Eudragit® RLPO relative to that of Eudragit® RSPO.

EXAMPLE 10

The compositions of Example 10 are obtained by the technique of extrusion according to the protocol described in Example 2, but in this case they contain 25 mg of N-[2-(7-methoxy-1-naphthyl)ethyl]acetamide and they are composed of a mixture comprising 30% active ingredient and 70% polymethacrylate.

EXAMPLE 11

The compositions of Example 11 are obtained as those of Example 6 but contain 100 mg of N-[2-(5-ethyl-1-benzothien-3-yl)ethyl]acetamide instead of fenspiride.

What is claimed is:

1. A solid controlled-release pharmaceutical composition, wherein the composition consists of a thermoformable mixture of at least one active ingredient and of one or more pH independent polymers selected from the group consisting of the polymethacrylates, the release of the active ingredient(s) being controlled solely by the nature of the polymethacrylate(s) used, by the amount thereof relative to the active ingredient(s), and by the technique of injection, coinjection, extrusion, or coextrusion employed in the manufacture of the composition.

2. A solid controlled-release pharmaceutical composition according to claim 1, wherein the polymethacrylate(s) used in the composition belong(s) to the family of the copolymers of ammonium methacrylate that consist of fully polymerized copolymers of acrylic acid and methacrylic acid ester having quaternary ammonium groups.

3. A solid controlled-release pharmaceutical composition according to claim 1, wherein the polymethacrylate(s) used in the thermoformable mixture is/are poly(ethyl acrylate, methyl methacrylate, trimethylaminoethyl methacrylate chloride)'s in the relative proportions of 1:2:0.2 and 1:2:0.1.

4. A solid controlled-release pharmaceutical composition according to claim 1, wherein the thermoformable mixture consists of poly(butyl methacrylate, (2-dimethylaminoethyl) methacrylate, methyl methacrylate) in the relative proportions of 1:2:1, alone or in combination with one or more polymethacrylate(s) selected from the group consisting of fully polymerized copolymers of acrylic acid and methacrylic acid ester having a small amount of quaternary ammonium groups and poly(ethyl acrylate, methyl methacrylate, trimethylaminoethyl methacrylate chloride)'s in the relative proportions of 1:2:0.2 and 1:2:0.1.

5. A solid controlled-release pharmaceutical composition according to claim 1, wherein the thermoformable mixture consists of poly(methacrylic acid, methyl methacrylate) in the relative proportions of 1:1, poly(methacrylic acid, methyl acrylate) in the relative proportions of 1:2, alone or in combination with one or more polymethacrylate(s) selected from the group consisting of fully polymerized copolymers of acrylic acid and methacrylic acid ester having a small amount of quatemary ammonium groups and poly (ethyl acrylate, methyl methacrylate, trimethylaminoethyl methacrylate chloride)'s in the relative proportions of 1:2:0.2 and 1:2:0.1, and poly(butyl methacrylate, (2-dimethylaminoethyl)methacrylate, methyl methacrylate) in the relative proportions of 1:2:1.

6. A solid controlled-release pharmaceutical composition according to claim 1, wherein the composition is administrable by one of the routes selected from the oral, buccal, sublingual, ocular, vaginal, rectal and parenteral routes.

7. A solid controlled-release pharmaceutical composition according to claim 1, wherein the composition is administrable by the oral route.

8. A solid controlled-release pharmaceutical composition according to claim 1, wherein the temperature of thermoforming of the mixture is 60° C. to 150° C.

9. A solid controlled-release pharmaceutical composition according to claim 8, wherein the temperature of thermoforming of the mixture is 80° C. to 130° C.

10. A solid controlled-release pharmaceutical composition according to claim 1, wherein the mixture is thermoformed according to the technique of extrusion.

11. A solid controlled-release pharmaceutical composition according to claim 1, wherein the mixture is thermoformed according to the technique of injection.

12. A solid controlled-release pharmaceutical composition according to claim 1, wherein the mixture is thermoformed according to the technique of coextrusion, the inner layer of the composition in this case being composed of the mixture and the outer layer of the composition being composed either of one or more polymethacrylate(s) or of one or more polymethacrylate(s) in admixture with one or more active ingredient(s), which may be the same as or different than that/those contained in the inner layer.

13. A solid controlled-release pharmaceutical composition according to claim 1, wherein the mixture is thermoformed according to the technique of coinjection, the central portion of the composition in this case being composed of the mixture and the outer layer of the composition being composed either of one or more polymethacrylate(s) or of one or more polymethacrylate(s) in admixture with one or more active ingredient(s), which may be the same as or different than that/those contained in the central portion.

14. A solid controlled-release pharmaceutical composition according to claim 1, wherein the composition optionally contains one or more pharmacologically acceptable excipients selected from anti-oxidants, flavorings, colorings, preservatives, sweeteners and anti-adherents.

15. A solid controlled-release pharmaceutical composition according to claim 1, wherein the active ingredient(s) is/are selected from anti-infective agents including penicillins, cephalosporins, cyclines, beta-lactamase inhibitors, aminosides, quinolones, nitroimidazole compounds, sulphamides or antibacterials, or antihistamines, anti-allergics, anaesthetics, steroidal or non-steroidal anti-inflammatories, antalgics having local or systemic action, antispasmodics, anti-cancer agents, diuretics, beta-blockers, antihypertensives, anti-angina agents, anti-arrythmics, vasodilators, bradycardiacs, calcium inhibitors, sedatives, cardiotonics, antifungals, antiulcerative agents, venotonics, vasculoprotectors, anti-ischaemics, antiemetics, anticoagulants, antithrombotics, immunosuppressors, immunomodulators, antivirals, antidiabetics, hypolipidaemic agents, antiobesity agents, anticonvulsants, hypnotics, antiparkinsonian agents, antimigraine agents, neuroleptics, anxiolytics, antidepressants, antipsychotics, psychostimulants, memory-enhancers, bronchodilators, antitussives, anti-osteoporotics, peptide hormones, steroids, enzymes, enzyme inhibitors, and melatoninergic agonists and antagonists.

16. A solid controlled-release pharmaceutical composition according to claim 1, wherein the active ingredient is benfluorex hydrochloride.

17. A solid controlled-release pharmaceutical composition according to claim 1, wherein the active ingredient is rilmenidine dihydrogenphosphate.

18. A solid controlled-release pharmaceutical composition according to claim 1, wherein the active ingredient is fenspiride hydrochloride.

19. A solid controlled-release pharmaceutical composition according to claim 1, wherein the active ingredient is (1R)-1-({[[(2R)-2-(acetylamino)-3-phenylpropanoyl] (cyclopentyl)amino]acetyl}amino)-4-{[amino(imino) methyl]amino}butylboronic acid hydrochloride.

20. A solid controlled-release pharmaceutical composition according to claim 1, wherein the active ingredient is gliclazide.

21. A solid controlled-release pharmaceutical composition according to claim 1, wherein the active ingredient is piribedil.

22. A solid controlled-release pharmaceutical composition according to claim 1, wherein the active ingredient is 2-({2-methoxy-2-[3-(trifluoromethyl)phenyl]ethyl}amino) ethyl-4-2-(2-{[2-(9H-fluoren-9-yl)acetyl]amino}ethyl) benzoate L-tartrate.

23. A solid controlled-release pharmaceutical composition according to claim 1, wherein the active ingredient is 3a,10-dihydro-5,5-dioxo-4H-(S)-pyrrolidino[1,2-c][1,2,4] benzothiadiazine.

24. A solid controlled-release pharmaceutical composition according to claim 1, wherein the active ingredient is N-[2-(5-ethyl-1-benzothien-3-yl)ethyl]acetamide.

25. A solid controlled-release pharmaceutical composition according to claim 1, wherein the active ingredient is indapamide.

26. A solid controlled-release pharmaceutical composition according to claim 1, wherein the active ingredient is tertatolol hydrochloride.

27. A solid controlled-release pharmaceutical composition according to claim 1, wherein the active ingredient is N-[2-(7-methoxy-1-naphthyl)ethyl]acetamide.

28. A solid controlled-release pharmaceutical composition, wherein the composition consists of a thermoformed mixture of at least one active ingredient and of one or more pH independent polymers selected from the group consisting of the polymethacrylates, the release of the active ingredient(s) being controlled solely by the nature of the polymethacrylate(s) used, by the amount thereof relative to the active ingredient(s), and by the technique of injection, coinjection, extrusion, or coextrusion employed in the manufacture of the composition at a temperature of 60° C. to 150° C.

29. The composition of claim 28, wherein the temperature employed is 80° C. to 130° C.

30. A solid controlled-release pharmaceutical composition, wherein the composition consists of a thermoformed mixture of at least one active ingredient and of at least two pH independent polymers selected from the group consisting of the polymethacrylates, the release of the active ingredient(s) being controlled solely by the nature of the polymethacrylate(s) used, by the amount thereof relative to the active ingredient(s), and by the technique of injection, co-injection, extrusion, or co-extrusion employed in the manufacture of the composition.

31. A composition of claim 30 wherein the polymethacrylates used in the composition are poly(ethyl acrylate, methyl methacrylate, trimethylaminoethyl methacrylate chloride)'s in the relative proportions of 1:2:0.2 and 1:2:0.1.

32. A composition of claim 30 wherein the polymethacrylates used in the composition belong to the families of copolymers of ammonium methacrylate that consist of fully polymerized copolymers of acrylic acid and methacrylic acid ester having quaternary ammonium groups.

33. A composition of claim 30 wherein the thermoformable mixture consists of poly(butylmethacrylate, (2-dimethylaminoethyl) methacrylate, methyl methacrylate) in the relative proportions of 1:2:1, alone or in combination with one or more polymethacrylate(s) selected from the group consisting of fully polymerized copolymers of acrylic acid and methacrylic acid ester having a small amount of quaternary ammonium groups and poly(ethyl acrylate, methyl methacrylate, trimethylaminoethyl methacrylate chloride)'s in the relative proportions of 1:2:0.2 and 1:2:0.1.

34. A composition of claim 30 wherein the thermoformable mixture consists of poly(methacrylic acid, methyl methacrylate) in the relative proportions of 1:1, and poly (methacrylic acid, ethyl acrylate) in the relative proportions of 1:1, alone or in combination with one or more polymethacrylate(s) selected from the group consisting of fully polymerized copolymers of acrylic acid and methacrylic acid ester having a small amount of quaternary ammonium groups and poly(ethyl acrylate, methyl methacrylate, trimethylaminoethyl methacrylate chloride)'s in the relative proportions of 1:2:0.2 and 1:2:0.1, and poly (butyl methacrylate, (2-dimethylaminoethyl)methacrylate, methyl methacrylate) in the relative proportions of 1:2:1.

35. A composition of claim 30 wherein the thermoformable mixture consists of poly(methacrylic acid, methyl methacrylate) in the relative proportions of 1:1, and poly (methacrylic acid, methyl methacrylate) in the relative proportions of 1:2, alone or in combination with one or more polymethacrylate(s) selected from the group consisting of fully polymerized copolymers of acrylic acid and methacrylic acid ester having a small amount of quaternary ammonium groups and poly(ethyl acrylate, methyl methacrylate, trimethylaminoethyl methacrylate chloride)'s in the relative proportions of 1:2:0.2 and 1:2:0.1, and poly(butyl methacrylate, (2-dimethylaminoethyl)methacrylate, methyl methacrylate) in the relative proportions of 1:2:1.

* * * * *